United States Patent [19]

Scholten

[11] Patent Number: 4,529,400
[45] Date of Patent: Jul. 16, 1985

[54] APPARATUS FOR NASO AND OROENDOTRACHEAL INTUBATION

[76] Inventor: James R. Scholten, 518 Mowbray Arch, Norfolk, Va. 23507

[21] Appl. No.: 592,876

[22] Filed: Mar. 23, 1984

[51] Int. Cl.³ ............................................. A61M 25/00
[52] U.S. Cl. ................................. 604/95; 128/207.14; 128/657
[58] Field of Search ............... 604/95, 170, 280; 128/207.14, 207.15, 200.26, 772, 657

[56] References Cited

U.S. PATENT DOCUMENTS

| | | | |
|---|---|---|---|
| 3,060,972 | 10/1962 | Sheldon | 128/772 X |
| 3,416,531 | 12/1968 | Edwards | 128/772 X |
| 3,521,620 | 7/1970 | Cook | 604/170 X |
| 4,329,983 | 5/1982 | Fletcher | 128/207.14 |

Primary Examiner—Stephen C. Pellegrino
Attorney, Agent, or Firm—Lalos, Leeds, Keegan, Marsh, Bentzen & Kaye

[57] ABSTRACT

A directable stylet for naso and oroendotracheal intubation including hand operated lever bar and grip support for applying high force to an articulating wire that produces a first curvature and a reverse curve to facilitate intubation. The stylet is covered with a plastic jacket to enable the stylet to be sterilized and therefore reused. The plurality of U-shaped links and a crossover link and a terminal link permits reverse curvature to be achieved during intubation.

26 Claims, 7 Drawing Figures

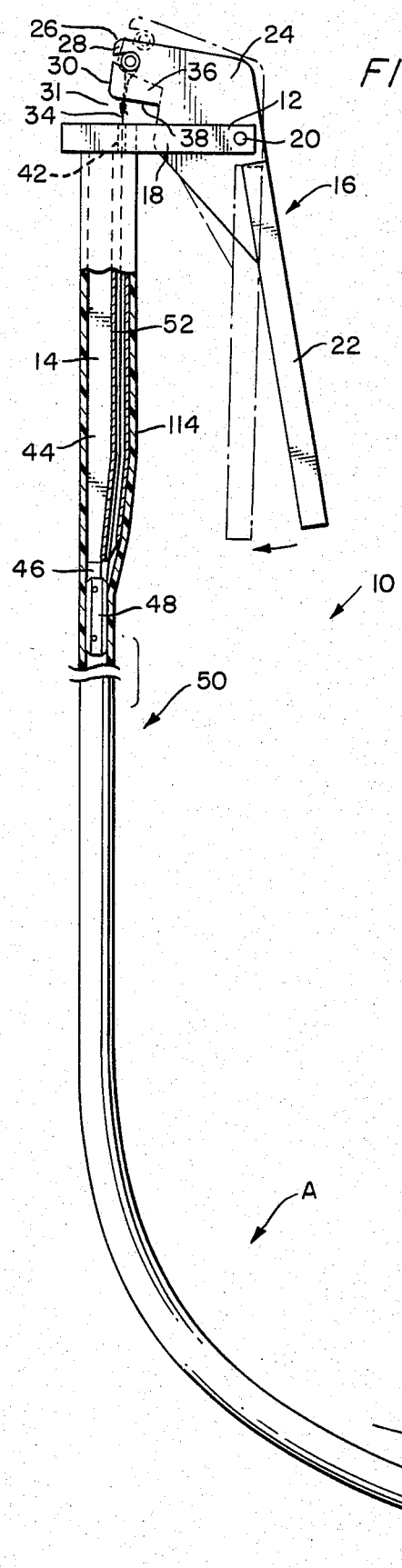
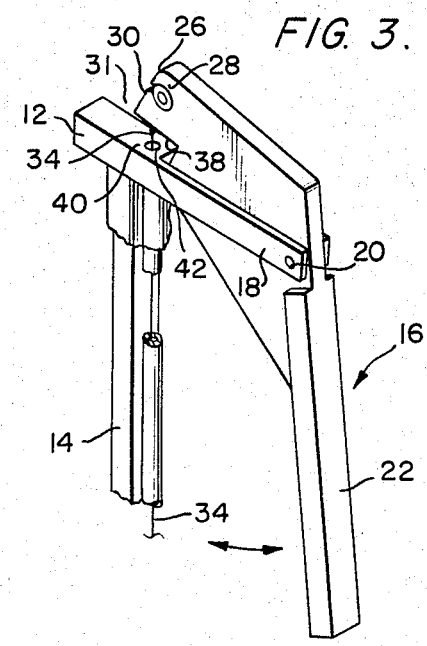
FIG. 2.
FIG. 3.

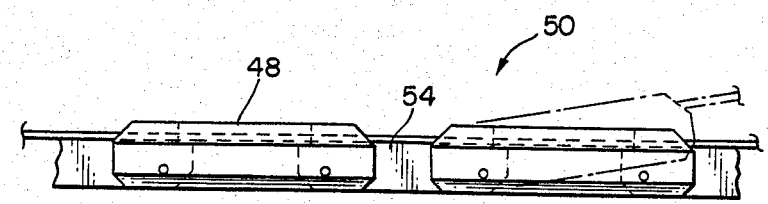
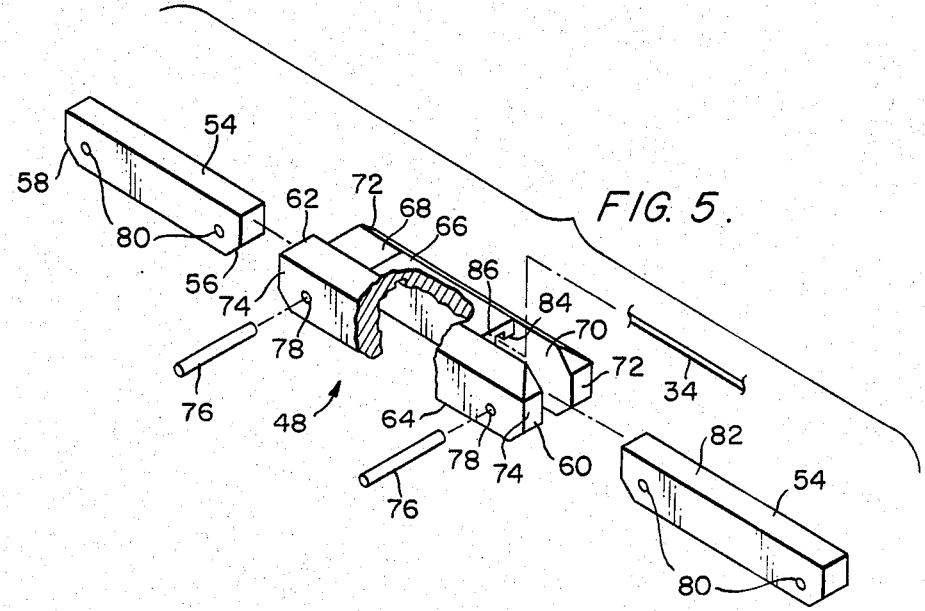
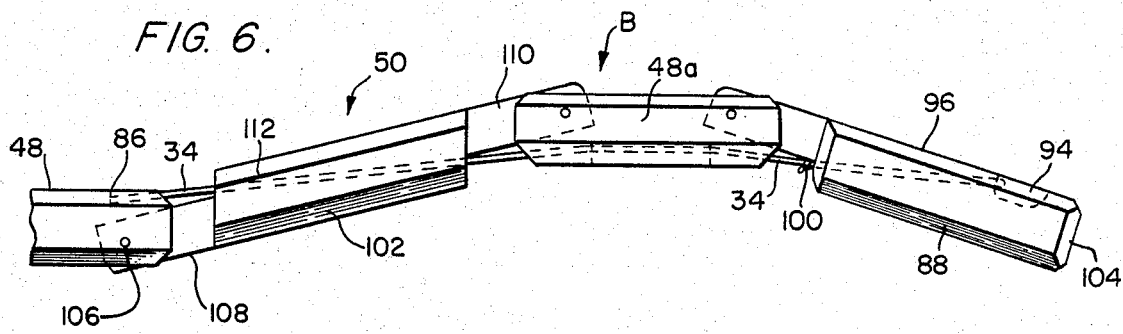
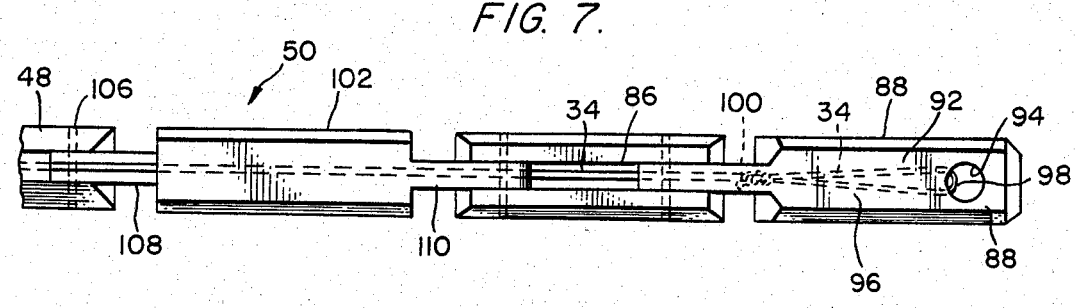

APPARATUS FOR NASO AND OROENDOTRACHEAL INTUBATION

OBJECTS OF THE INVENTION

A principal object of this invention is the provision of an improved directable stylet used to facilitate intubation of the trachea with an endotracheal tube.

A further object is the provision of directable stylets to facilitate intubation, in trauma victims where the neck may not be manipulated.

A further object is the provision of directable stylets to facilitate intubations in patients with relatively short and/or fat necks.

A further object is the provision of directable stylets to facilitate intubations and can easily generate sufficient force to direct a concentric endotracheal tube without protruding past the tubes distal tip.

A further object is the provision of directable stylets that do not require the typical gas sterilization that would minimize the availability of the stylet.

A further object is the provision of directable stylets that will simultaneously lift and point downwardly the anterior tip of the surrounding endotracheal tube in order to pass through the widest opening between the vocal cords and avoid misdirection into the esophagus rather than the intended trachea.

A further object is the provision of directable stylets to facilitate blind intubations which enable the user to apply a high force to effect the direction of the stylet.

This invention also has as a further object the provision of directable stylets that are reusable and storable in sterilizing fluid until use on demand.

BRIEF DESCRIPTION OF THE DRAWINGS

FIG. 2 is a side view partly broken away of the directable stylet illustrating in phantom lines the range of movement attainable.

FIG. 3 is a partially cut away perspective view of the handle end of the stylet.

FIG. 4 is a side elevational view partially broken away of the links and connecting bars.

FIG. 5 is an exploded perspective view of the links and connecting bars.

FIG. 6 is a side elevational view partly broken away of the distal end of the chain of pivotably connected links.

FIG. 7 is a top view partially broken away of the distal end of the chain of pivotably connected links.

DETAILED DESCRIPTION OF THE PRESENT INVENTION

Figure 1:
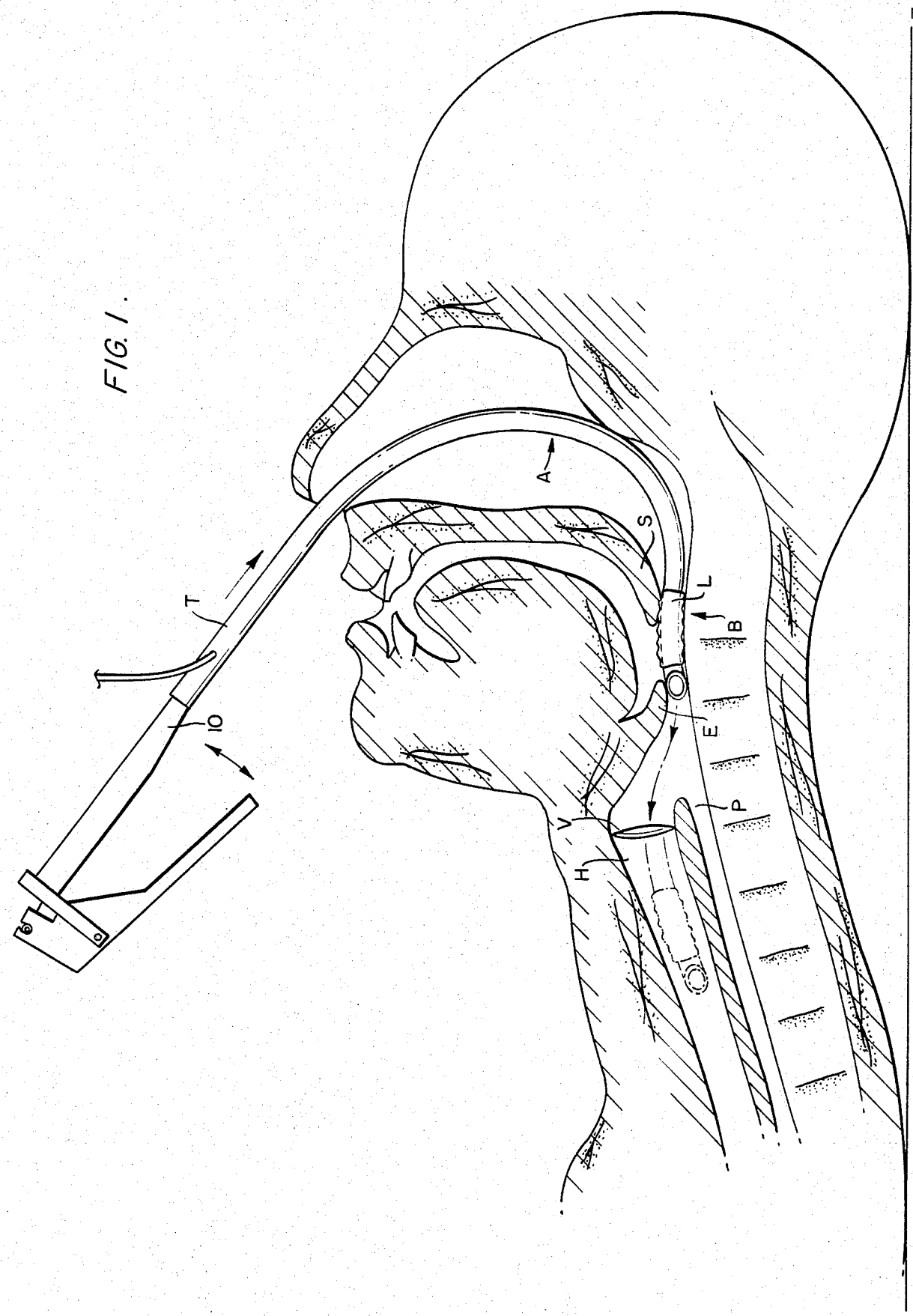
FIG. 1 is a diagrammatic view of a nasal tracheal intubation using the directable stylet of the present invention on a patient.

The present invention as shown generally in FIGS. 2 and 3 of the drawing is a stylet 10 that may be used for intubations such as tube T into the trachea whether through the nose or through the mouth. The stylet is composed of several unique features that in general include a base 12, a grip support 14 secured to the underside of the base 12 and a lever bar 16 pivotally mounted on one end of the base by being received within links 18 formed from a bifurcation of the base as best shown in FIG. 3. The lever bar is pivoted to the base with the aid of pivot pin 20 which passes through both legs and a suitable bore, not shown, in lever bar 16.

The lever bar 16 is provided with an enlongated extension 22 forming a handle at the other end of the lever bar 16 and on the other side of pivot pin 20. The lever bar 16 takes the form of a doghead 24 having a jaw 26 positioned at a portion of the doghead 24 remote from the pivot pin 20. The jaw 26 is composed of spaced upper and lower jaw members 28 and 30 spaced from each other to form a jaw opening 31. Holding pin 32 is received within the jaw opening 31 for the purpose of securing in position an articulating wire 34 which is suitably secured to the holding pin 32 and passes through an accommodating bore 36 positioned within the lower jaw member 30. The underside of the lower jaw member 30 is provided with an abutment 38 to limit the pivotal movement of the doghead 24 about pivot pin 20 by abutting the top surface 40 of the base 12.

A bore 42 is extended through the base 12 as best shown in FIG. 3. The bore 42 receives the articulating wire 34 as it passes through the base 12 and enters into the elongated grip support 14 for passage down through the length of the stylet 10 as will be further described.

The grip support 14 depends from the underside of the base 12 and is composed of a depending rod-like member 44 which preferably extends below the base 12 a length sufficient to accommodate at least several fingers of the hand of the user.

The construction is such that handle 22 moves toward and away from the grip support 14 in a common plane as shown in phantom lines in FIG. 2. As the handle 22 and the grip support 14 are brought closer together, it is manifest that the articulating wire 34 is raised. Because of the grip support and handle far greater force can be applied to lift the wire than previously possible.

At the base of the rod 44 there is provided a rod extension 46 for pivoted connection with the uppermost link 48 of a plurality of links forming chain 50 of the stylet 10. Positioned as a guide for the articulating wire 34 as it depends from the base 12 through the bore 42, is an enclosed rod passageway 52 that is preferably integral with and extends the length of the rod 44. It is also contemplated that the rod 44 and the rod passageway 52 may be a single integral tubular member to the end of which is formed rod extension 46 as previously described. Providing the rod passageway 52 as a separate and distinct passageway, as shown, or in a single tubular member forming the grip support 14 are equivalent alternatives.

As best shown in FIGS. 4 and 5 the chain 50 is composed of a plurality of links 48 interconnected by individual bars 54. The bars are shown to be solid material in the form of a rectangular prism but having the lower corners as shown in FIG. 5 at 56 and 58 beveled to permit freedom of pivoting of the bar 54 about the link 48. The link 48 is preferably formed in an elongated U-shape having a top and bottom portions 60 and 62 and an open front 64 and is partially closed back 66 leaving openings in the back at 68 and 70. The partially closed back and the openings 68 and 70 form a pair of protruding fingers 72 and 74 at each end of the link 48 to which the bar 54 is inserted. Pivot pin 76 is inserted through suitable bores 78 in the ends of the fingers which coincide with similar bores 80 at the ends of the rods 54. The positioning of the rod 54 within the fingers 72 and 74 of the link 48 is such that a spacing is provided between the top 82 of the rod 54 and the underside 84 of the closed back 66 to accommodate the articulating wire 34 which passes therebetween. To contain and control the positioning of the wire 34 a suitable groove 86 is provided to extend the length of the back 66. The groove 86 stabilizes and positions the articulating wire 34 to guide it as it slides longitudinally forwardly and backwardly between the link 48 and the rod 54.

In FIGS. 6 and 7 there is shown one of the unique aspects of the present invention that enables the stylet to not only achieve the usual curve in the stylet as shown at A but also to achieve a change in curvature which may simply be a flattening or a reverse curve as shown at B of FIG. 2. The curves A and B are coplanar as shown in FIGS. 6 and 7 the articulating wire 34 is secured to a terminal link 88 which may be a solid bar but has a dual diverging pair of passageways 90 and 92 to receive the wire 34. The dual passageways 90 and 92 exit at opening 94 on the undersurface 96 of the terminal link 88. The opening 94 allows the articulating wire 34 to be turned 180 degrees as shown at the bend 98 and secured to itself as in a knot as shown in FIGS. 6 and 7 at 100. In order to achieve the reversing direction of the stylet as shown at B in FIG. 2 and FIG. 6 a reversing or crossover link 102 is positioned usually within about 10 centimeters from the working tip 104 of the terminal link 88. More preferably 3 to 7 centimeters would be desirable as measured from the working end 104 of the terminal link 88 to the remote pivot point 106 of the crossover link 102, as shown in FIGS. 6 and 7.

The crossover link 102 as shown is a solid bar similar to that of terminal link 88 and is provided with extensions 108 and 110, each of which protrudes from the body of the crossover link 102 as best shown in FIGS. 6 and 7. The body of crossover link 102 is provided with a unique diagonal passageway 112 for receiving the articulating wire 34. The purpose of the diagonal passageway 112 is to set up a lever action due to the offset of the diagonal passageway 112 that in FIG. 6 permits link 48 to follow the curvature A of FIG. 2 but also provide for a reverse lever action and permit link 48a between the crossover link 102 and terminal link 88 to achieve a reverse or flattened curve as shown at B in FIG. 6 and in FIG. 2. Terminal link 8 will attain in part the positioning of curve B by reason of the articulating wire 34 being secured to the surface 96.

As another feature of the present invention there is provided as best shown in FIG. 2 a plastic jacket or coating 114 that may be shrink fitted over the stylet to protect and preserve the stylet and eliminate the need for gas sterilization which is a common requirement for prior art stylets. As shown the plastic coating 114 extends from the undersurface of the base 12 and covers the entire length of the chain 50 of the stylet 10 and yet is flexible enough to be able to form the curves A and B as shown in FIG. 2. The plastic coating may be any common liquid impervious plastic such as polyethylene, polypropylene or the like or may even be a rubber composition. The primary purpose of the coating 114 is simply to enable the stylet to be sterilized by immersion in the sterilizing liquid rather than the requirement for gas sterilization.

It should be manifest upon careful reading of the detailed description how the present invention is utilized and therefore a short outline should suffice.

FIG. 1 illustrates the use of the stylet 10 for insertion of the tube T that may have the inflatable balloon L at one end as shown. As the stylet with the surrounding tube is inserted through the nose and down through the throat and the control means in the form of lever 16 and grip support 14 are brought closer together by manual pressure of the user, the links 48 are articulated and the stylet takes on the general configuration of curve A so that it is able to pass down behind the soft palate S of the subject, then with continued and higher pressure being more easily applied with the combination handle and grip support, the stylet begins to take on a reverse curve at B. By reason of the crossover link reversing the torque applied through the articulating wire 34, the links 48a and 88 attain a different direction within the same plane as curve A. The attainment of this reverse curve is particularly desirable in order not to enter the dead end in front of the epiglottis but rather continue on down behind the epiglottis towards and through the widest opening in the vocal cords V, avoid the esophagus P, and continue on into the trachea H as shown in the phantom lines. At that time balloon B may be inflated in the conventional manner.

It should be apparent that all the objects of the present invention have been met through the device as fully described and shown and that the scope of the invention should be limited solely by the following claims.

I claim:

1. A directable stylet for endotracheal tubes comprising:
   (a) a base;
   (b) an elongated grip support depending from said base; (c) a lever bar pivotably mounted on said base to pivot substantially in the plane of said elongated grip support;
   (d) a plurality of links pivotably interconnected to form a chain wherein said links are operably connected to said base; and
   (e) an articulating wire connected at one end to said lever bar and at the other end to the terminal link in said chain remote from said base, and passing through intermediate links wherein application of force to said lever bar causes said links to articulate substantially in the plane of said grip support in order to facilitate the control of said endotracheal tube.

2. The directable stylet for endotracheal tubes, as recited in claim 1, wherein said chain depends from the end of said grip support remote from said base.

3. The directable stylet for endotracheal tubes, as recited in claim 1, wherein said base includes a bore and said articulating wire passes through said bore in said base for connection to said lever bar.

4. The directable stylet for endotracheal tubes, as recited in claim 3, including an axial channel provided within said grip support and said articulating wire being slidably disposed in said channel, and said axial channel being so positioned to register with said bore in said base, and wherein said chain pivotably depends from the end of said grip support remote from said base.

5. The directable stylet for endotracheal tubes, as recited in claim 1, further comprising a continuous flexible substantially impervious jacket conforming to the outer surface of said chain.

6. The directable stylet for endotracheal tubes, as recited in claim 5, wherein said jacket extends from the tip of said terminal link along said chain to at least the point where said chain is operably connected to said base.

7. The directable stylet for endotracheal tubes, as recited in claim 1, wherein said base is bifurcated and wherein said lever bar is pivotably mounted therebetween.

8. The directable stylet for endotracheal tubes, as recited in claim 1, wherein said articulating wire extends substantially the length of said chain and is slidably disposed within each of the intermediate links of said chain.

9. A directable stylet for endotracheal tubes comprising:
   (a) a base;
   (b) a plurality of links pivotably interconnected to form a chain and being operably connected to said base;
   (c) control means secured to said base for controlling the movement of said chain;
   (d) an articulating wire operatively connected at one end to said control means and at the other end to the terminal link and passing through intermediate links of said chain for articulating said chain; and
   (e) reversing means operatively connected intermediate the ends of said chain for reversing the direction of articulation whereby upon force being applied by said control means said chain articulates primarily in a first direction and wherein continued application of said force activates said reversing means to articulate the end of said chain in a second direction.

10. The directable stylet for endotracheal tubes, as recited in claim 9, wherein said reversing means includes a reversing link for changing direction of said force along said chain.

11. The directable stylet for endotracheal tubes, as recited in claim 10, wherein each of said links includes a passageway for said wire, said passageway being disposed primarily on one side of said chain above said reversing means and on the other side of said chain below said reversing means.

12. The directable stylet for endotracheal tubes, as recited in claim 11, wherein said reversing link includes a canted passageway therethrough to receive said wire and reverse the direction of said force.

13. The directable stylet for endotracheal tubes, as recited in claim 10, wherein said reversing link is positioned proximate to the free end of said chain.

14. The directable stylet for endotracheal tubes, as recited in claim 13, wherein said first and said second directions are coplanar.

15. The directable stylet for endotracheal tubes, as recited in claim 14 including,
   an elongated grip support depending from said base,
   a lever bar pivotably mounted on said base to pivot substantially in the plane of said elongated grip support, and
   a bore and said articulating wire passes through said bore in said base for connection to said lever bar.

16. The directable stylet for endotracheal tubes, as recited in claim 14 including,
   an elongated grip support depending from said base,
   a lever bar pivotably mounted on said base to pivot substantially in the plane of said elongated grip support,
   a bore and said articulating wire passes through said bore in said base for connection to said lever bar, and
   a continuous flexible substantially impervious jacket conforming to the outer surface of said chain.

17. The directable stylet for endotracheal tubes, as recited in claim 9 including,
   an elongated grip support depending from said base, and
   a lever bar pivotably mounted on said base to pivot substantially in the plane of said elongated grip support.

18. The directable stylet for endotracheal tubes, as recited in claim 17, wherein said base includes a bore and said articulating wire passes through said bore in said base for connection to said lever bar.

19. The directable stylet for endotracheal tubes, as recited in claim 9, further comprising a continuous flexible substantially impervious jacket conforming to the outer surface of said chain.

20. A directable stylet for endotracheal tubes comprising:
   (a) a base;
   (b) a plurality of links pivotably interconnected to form a chain and being operably connected to said base;
   (c) control means secured to said base for controlling the movement of said chain;
   (d) an articulating wire operatively connected at one end to said control means and at the other end to the terminal link and passing through intermediate links of said chain for articulating said chain;
   (e) said links including a U-shaped elongated link having a front, back, top and bottom portions, said front portion being open and said back portion having a back panel and being at least partially closed, said top and bottom portions including pivot means; and
   (f) said links also including a bar link interconnecting said U-shaped links and being connected at said pivot means to said U-shaped links.

21. The directable stylet for endotracheal tubes, as recited in claim 20 including,
   said bar link and said back panel forming a passageway for said wire extending the length of said chain.

22. The directable stylet for endotracheal tubes, as recited in claim 21 including,
   said passageway being offset relative to the axis of said chain.

23. The directable stylet for endotracheal tubes, as recited in claim 20 including,
   reversing means operatively connected intermediate the ends of said chain for reversing the direction of articulation whereby upon force being applied by said control means said chain articulates primarily in a first direction and wherein continued application of said force activates said reversing means to articulate the end of said chain in a second direction.

24. The directable stylet for endotracheal tubes, as recited in claim 23 including,
   said reversing links includes a canted passageway therethrough to receive said wire and reverse the direction of said force.

25. The directable stylet for endotracheal tubes, as recited in claim 24 including,
   said reversing link is positioned proximate to the free end of said chain whereby upon force being applied by said control means said chain articulates primarily in a first direction and wherein continued application of said force activates said reversing means to articulate the end of said chain in a second direction.

26. The directable stylet for endotracheal tubes, as recited in claim 25 including,
   said first and said second directions are coplanar.

* * * * *